US010881678B2

(12) United States Patent
Levitt

(10) Patent No.: US 10,881,678 B2
(45) Date of Patent: Jan. 5, 2021

(54) CYTOTOXIC AGENTS FOR THE TREATMENT OF CANCER

(71) Applicant: CytRx Corporation, Los Angeles, CA (US)

(72) Inventor: Daniel Levitt, San Francisco, CA (US)

(73) Assignee: CytRx Corporation, Los Angeles, CA (US)

(*) Notice: Subject to any disclaimer, the term of this patent is extended or adjusted under 35 U.S.C. 154(b) by 0 days.

(21) Appl. No.: 16/279,737

(22) Filed: Feb. 19, 2019

(65) Prior Publication Data

US 2019/0350952 A1 Nov. 21, 2019

Related U.S. Application Data

(63) Continuation of application No. 14/893,821, filed as application No. PCT/US2014/040872 on Jun. 4, 2014, now Pat. No. 10,278,981.

(60) Provisional application No. 61/831,219, filed on Jun. 5, 2013.

(51) Int. Cl.
| | |
|---|---|
| *A61K 31/704* | (2006.01) |
| *A61K 45/06* | (2006.01) |
| *C07H 15/26* | (2006.01) |
| *A61K 47/54* | (2017.01) |
| *A61P 35/04* | (2006.01) |
| *A61P 35/02* | (2006.01) |
| *A61P 35/00* | (2006.01) |
| *A61P 25/00* | (2006.01) |

(52) U.S. Cl.
CPC ............ *A61K 31/704* (2013.01); *A61K 45/06* (2013.01); *A61K 47/545* (2017.08); *A61P 25/00* (2018.01); *A61P 35/00* (2018.01); *A61P 35/02* (2018.01); *A61P 35/04* (2018.01); *C07H 15/26* (2013.01)

(58) Field of Classification Search
CPC .... A61K 31/704; A61K 45/06; A61K 47/545; A61P 25/00; A61P 35/00; A61P 35/02; A61P 35/04; C07H 15/26
See application file for complete search history.

(56) References Cited

U.S. PATENT DOCUMENTS

| | | | |
|---|---|---|---|
| 4,840,938 A | 6/1989 | Gatti et al. | |
| 7,387,771 B1 | 6/2008 | Kratz | |
| 7,902,144 B2 | 3/2011 | Kratz | |
| 8,153,581 B2 | 4/2012 | Kratz | |
| 8,703,724 B2 | 4/2014 | Kratz | |
| 8,846,602 B2 | 9/2014 | Kratz | |
| 10,278,981 B2 | 5/2019 | Levitt | |
| 2001/0036444 A1 | 11/2001 | Placke et al. | |
| 2003/0013666 A1 | 1/2003 | Gatti et al. | |
| 2005/0148534 A1 | 7/2005 | Castellino et al. | |
| 2010/0172844 A1 | 7/2010 | Neri et al. | |
| 2012/0135914 A1 | 5/2012 | Demeule et al. | |

FOREIGN PATENT DOCUMENTS

| | | |
|---|---|---|
| CN | 101897667 A * | 12/2010 |
| CN | 102245636 | 11/2011 |
| CN | 102939109 | 2/2013 |
| WO | WO 2008/138646 | 11/2008 |
| WO | WO 2011/131314 | 10/2011 |
| WO | WO 2014/093815 | 6/2014 |

OTHER PUBLICATIONS

Google Machine Translation of CN101897667A, https://patents.google.com/patent/CN101897667A/en?oq=101897667, accessed online on Oct. 28, 2020 (Year: 2020).*
"NCT01706835 on 20112_11_05: ClinicalTrials.gov Archive", retrieved from the Internet: https://clinicaltrials.gov/arcive/NCT01706835/ 2012 11 05 (Nov. 5, 2012).
Brandes et al., "New drugs in recurrent high grade gliomas," Anticancer Res., 3B:1913-1920 '2000).
DeAngelis, "Brain Tumors," N. Engl J Med, 31!4: 114-123 (2001).
Elsadek al., J. Controlled Release, 2012, 157, p. 4-28.
Gabathuler, et al., "Development of new peptide vectors for the transport of therapeutic across the blood-brain barrier", Therapeutic Delivery 1(4): 571-586 (Oct. 1, 2010).
Huncharek et al., "Multi-drug versus single agent chemotherapy for high grade astrocytoma; results of a meta-analysis," Anticancer Res., 18: 4693-4697 (1998).
Komblith et al., "Chemotherapy for malignant gliomas," J. Neurosurg. 68: 1-17 (1988).
Kratz et al., "Acute and repeat-dose toxicity studies of the (6-maleimidocaproyl)hydrazone derivative of doxorubicin (DOXO-EMCH), an albumin-binding prodrug of the anticancer agent doxorubicin," Hum Exp Toxicol, 26:19-35 (2007).
Kratz et al., "Drug-polymer conjugates containing acid-cleavable bonds," Grit Rev Ther Drug Carrier Syst., 16:245-88 (1999).
Kratz et al., "Probing the cysteine-34 position of endogenous serum albumin with thiol-binding doxorubicin derivatives. Improved efficacy of an acid-sensitive doxorubicin derivative with specific albumin-binding properties compared to that of the parent compound," J Med Chem, 45:5523-5533 (2002).
Kratz et al., J. Controlled Rel., 2008, 132, p. 171-183.
Natale, et al., "Pharmacokinetic study of aldoxorubicin in solid tumors patients", 49th Annu. Meet. Am. Soc. Clin. Oncol. (A, Jan. 1, 2013).

(Continued)

*Primary Examiner* — Jonathan S Lau
(74) *Attorney, Agent, or Firm* — Sheridan Ross P.C.

(57) ABSTRACT

The present invention relates to a method of treating brain cancer comprising administering a therapeutically effective substance to a patient, wherein the therapeutically effective substance comprises: (I), or a pharmaceutically acceptable salt thereof, wherein X is a moiety that can be cleaved hydrolytically or enzymatically in the body of the patient in a pH-dependent manner.

9 Claims, 13 Drawing Sheets

(56) References Cited

OTHER PUBLICATIONS

Nelson et al., "Survival and prognosis of patients with astrocytoma with atypical or anaplastic features," J. Neurooncol., 3: 99-103 (1985].

Rousselle, et al., "New advances in the transport of doxorubicin through the blood-brain barrier by a peptide vector-mediated strategy", Molecular Pharmacology, p. 679-686 (Apr. 1, 2000).

Sandi et al., "Detection of doxorubicin hydrochloride accumulation in the rat brain after morphine treatment by mass spectrometry," Cancer Chemother. Pharmacol., 67: 1333-1340 (2011).

Schwartzbaum et al., J. Neuro-Oncol., 1999, 43, p. 35-41.

Stan et al., "Doxorubicin-induced cell death in highly invasive human gliomas," Anticancer Res., 19: 941-950 (19991.

Steiniger et al., "Chemotherapy of glioblastoma in rats using doxorubicin-loaded nanoparticles," Int. J. Cancer, 109: 759-767 (2004).

Von Hoist, "Uptake of adriamycin in tumour and surrounding brain tissue in patients with malignant gliomas," Acta Neurochir., 104: 13-16 (1990).

Willner et al., "(6-Maleimidocaproyl)hydrazone of doxorubicin—a new derivative for the oreoaration of immunoconiuaates of doxorubicin," Bioconivaate Chem, 4:521-527 (19931.

Yang et al., Int. J. Nanomed., 2012, 7, p. 965-974.

Official Action for U.S. Appl. No. 14/893,821 dated Feb. 27, 2017, 10 pages.

Official Action for U.S. Appl. No. 14/893,821 dated Oct. 30, 2017, 10 pages.

Official Action for U.S. Appl. No. 14/893,821 dated Apr. 27, 2018, 13 pages.

Notice of Allowance for U.S. Appl. No. 14/893,821 dated Nov. 21, 2018, 13 pages.

CAPLUS Accession No. 2013:1139322, 2013, 1 page.

Official Action for European Patent Application No. 14807006.3 dated Nov. 29, 2019, 6 pages.

Official Action for European Patent Application No. 14807006.3 dated Apr. 24, 2020, 5 pages.

Graeser et al., "INNO-206, the (6-maleimidocaproyl hydrazone derivative of doxorubicin), shows superior antitumor efficacy compared to doxorubicin in different tumor xenograft models and in an orthotopic pancreas carcinoma model," Invest New Drugs, 2010, vol. 28, pp. 14-19.

Official Action for Canadian Patent Application No. 2,912,908 dated May 26, 2020, 6 pages.

Official Action for Korean (English translation) Patent Application No. 10-2015-7036829 dated Aug. 26, 2020, 19 pages.

\* cited by examiner

CYTOTOXIC AGENTS FOR THE TREATMENT OF CANCER

CROSS REFERENCE TO RELATED APPLICATIONS

This application is a continuation of U.S. application Ser. No. 14/893,821, filed Nov. 24, 2015, now U.S. Pat. No. 10,278,981, which is a national stage application under 35 U.S.C. 371 and claims the benefit of PCT Application No. PCT/US2014/040872 having an international filing date of Jun. 4, 2014, which designated the United States, which PCT application claimed the benefit of U.S. Provisional Application No. 61/831,219, filed Jun. 5, 2013, the disclosures of each of which are herein incorporated by reference in their entireties.

BACKGROUND OF THE INVENTION

Anthracyclines are a class of antibiotics derived from certain types of *Streptomyces* bacteria. Anthracyclines are often used as cancer therapeutics and function in part as nucleic acid intercalating agents and inhibitors of the DNA repair enzyme topoisomerase II, thereby damaging nucleic acids in cancer cells, preventing the cells from replicating. One example of an anthracycline cancer therapeutic is doxorubicin, which is used to treat a variety of cancers including breast cancer, lung cancer, ovarian cancer, lymphoma, and leukemia. The 6-maleimidocaproyl hydrazone of doxorubicin (DOXO-EMCH also known as aldoxorubicin or INNO-206) was synthesized to provide an acid-sensitive linker that could be used to prepare immunoconjugates of doxorubicin and monoclonal antibodies directed against tumor antigens (Willner et al., Bioconjugate Chem 4:521-527 (1993)). In this context, antibody disulfide bonds are reduced with dithiothreitol to form free thiol groups, which in turn react with the maleimide group of DOXO-EMCH to form a stable thioether bond. When administered, the doxorubicin-antibody conjugate is targeted to tumors containing the antigen recognized by the antibody. Following antigen-antibody binding, the conjugate is internalized within the tumor cell and transported to lysosomes. In the acidic lysosomal environment, doxorubicin is released from the conjugate intracellularly by hydrolysis of the acid-sensitive hydrazone linker. Upon release, the doxorubicin reaches the cell nucleus and is able to kill the tumor cell. For additional description of doxorubicin and DOXO-EMCH see, for example, U.S. Pat. Nos. 7,387,771 and 7,902,144 and U.S. patent application Ser. No. 12/619,161, each of which is incorporated in their entirety herein by reference.

Further, DOXO-EMCH has been conjugated in vitro with human serum albumin (HSA) to form a stable thioether conjugate (Kratz et al., J Med. Chem 45:5523-5533 (2002)).

Brain tumors, including malignant gliomas in particular, are among the most aggressive human cancers and are rarely curable (DeAngelis et al., N. Engl. J. Med. 2001, 344, 114-123; Nelson et al., J. Neurooncol. 1985, 3, 99-103; Kornblith et al., J. Neurosurg. 1988, 68, 1-17). The median survival after diagnosis is about 12-14 months. Treatment with chemotherapeutic drugs such as nitrosoureas, platinum compounds, and temozolomide, increases the survival time of patients only marginally (Huncharek et al., Anticancer Res. 1998, 18, 4693-4697; Brandes et al., Anticancer RES. 2000, 20, 1913-1920). Further complicating treatment of brain cancers is the inability of many drugs to cross the blood-brain barrier (BBB). The BBB consists of tight junctions around the capillaries and protect the brain against changes in the levels of certain substances like ions, or against infections. The endothelial cells restrict the diffusion of large molecules such as albumin, while allowing the diffusion of smaller molecules such as $O_2$ or $CO_2$. Glioblastoma cell lines were driven to apoptosis following growth arrest induced by doxorubicin (Stan et al., Anticancer Res., 1999, 19, 941-950). However, doxorubicin lacks the ability to cross the BBB, because it is a substrate of the P-glycoprotein efflux pumps (Sardi et al., Cancer Chemother. Pharmacol., 2011, 67, 1333-1340). Free doxorubicin concentration in glioma tissues is below effective levels and doxorubicin has no effect on glioblastoma growing in the brain (Steiniger et al., Int. J. Cancer, 2004, 109, 759-767; Von Hoist, Acta Neurochirr., 1990, 104, 13-16). Therefore, the development of a strategy allowing drug delivery across the BBB is of prime importance. Hence, the need for efficient carriers to transport anticancer drugs, such as doxorubicin, into the brain remains high.

SUMMARY OF THE INVENTION

The present invention is based on the surprising observation that when administered intravenously, a therapeutically effective substance (e.g., DOXO-EMCH) induces tumor regression in and significantly increases survival of a mammal suffering from a brain tumor such as e.g., glioblastoma multiforme tumors.

The present invention relates to a method for the treatment of brain cancer comprising administering a therapeutically effective substance to a patient, wherein the therapeutically effective substance comprises the structure as in FIG. 13, or a pharmaceutically acceptable salt thereof wherein X is a bond that can be cleaved hydrolytically or enzymatically in the body of the patient in a pH-dependent manner.

In some embodiments, the moiety X is cleaved in the body of the patient, thereby releasing the cytotoxic agent. In some embodiments, the cytotoxic agent is an anthracycline. In some embodiments, the anthracycline is selected from a group consisting of doxorubicin, daunorubicin, epirubicin, idarubicin, valrubicin, pirarubicin, zorubicin, aclarubicin, caminomycin, mitoxantrone and ametantrone, or a derivative of any of the foregoing, or a pharmaceutically acceptable salt of any of the foregoing. In some embodiments, the anthracycline is doxorubicin or a pharmaceutically acceptable salt thereof. In some embodiments, the covalently protein-binding group is selected from the group consisting of maleimide, haloacetamide, haloacetate, pyridylthio, N-hydroxysuccinimide ester, isothiocyanate, disulfide, vinylcarbonyl, aziridine and acetylene. In some embodiments, the covalently protein-binding group is maleimide. In some embodiments, the linker comprises an organic molecular residue, which contains at least one aliphatic carbon chain, or an aliphatic carbon ring having 1-12 carbon atoms, some of which can be replaced with heteroatoms, or an aromatic moiety. In some embodiments, the linker comprises at least one carbon chain having 1-12 carbon atoms. In some embodiments, the cytotoxic agent and the linker are joined by a hydrazone moiety. In some embodiments, the therapeutically effective substance has the following structure:

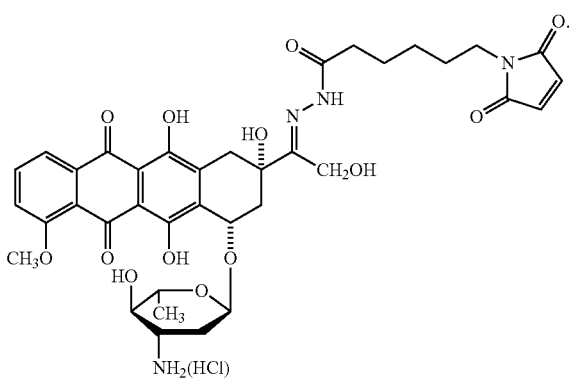

In some embodiments, the brain cancer is a primary brain cancer. In some embodiments, the primary brain cancer is glioma, astrocytoma, oligodendroglioma, ependymoma, meningioma, craniopharyngioma, germinoma, pineocytoma, pineoblastoma and glioblastoma multiforme. In some embodiments, the primary brain cancer is glioblastoma multiforme. In some embodiments, the brain cancer is a secondary or metastatic cancer. In some embodiments, the secondary or metastatic cancer is selected from bladder cancer, breast cancer, lung cancer, stomach cancer, endometrial cancer, ovarian cancer, pancreatic cancer, pancreatic ductal adenocarcinoma, cancer of the adrenal cortex, non-Hodgkin's lymphoma, multiple myeloma, leukemia, Kaposi's sarcoma, Ewing's sarcoma, soft tissue sarcoma, nephroblastoma, prostate cancer, liver cancer, bone cancer, chondrosarcoma, renal cancer, bladder cancer, thyroid cancer and gastric cancer. In some embodiments, the cancer is a temozolomide-resistant cancer. In some embodiments, the temozolomide-resistant cancer is a temozolomide-resistant glioblastoma multiforme.

In some embodiments, the therapeutically effective substance is administered in combination with an anti-cancer agent. In some embodiments, the anti-cancer agent is selected from doxorubicin, cisplatin, carboplatin, paclitaxel, docetaxel, temozolomide, nitrosoureas, bortezomib, gemcitabine, etoposide, topotecan, or a pharmaceutically acceptable salt thereof.

Upon administration, the therapeutically effective substance binds covalently, by way of the protein-binding molecule, to body fluid constituents or tissue constituents, thereby creating a transport form of the cytotoxic agent which can be hydrolytically or enzymatically cleaved, in a pH-dependent manner, in the body with the cytotoxic agent being released. Because of their protein-binding properties, injectable medicament preparations are obtained of therapeutically effective substances that decisively alter and improve the pharmacokinetic profile of the cytotoxic agent. When the therapeutically effective substance of the invention interacts with body fluids, it binds covalently to body fluid or tissue constituents, preferably to serum proteins, more preferably to serum albumin, in order to yield macromolecular prodrugs which transport the cytotoxic agent to the target site and/or release it in a metered form.

In some embodiments, the brain cancer is a primary brain tumor. In some embodiments, the primary brain tumor is glioblastoma multiforme. In other embodiments, the brain cancer is a metastatic brain tumor. In some embodiments, the metastatic tumor is from a cancer including but not limited to breast cancer, lung cancer, stomach cancer, endometrial cancer, ovarian cancer, pancreatic cancer, pancreatic ductal adenocarcinoma, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, thyroid cancer and gastric cancer. In some embodiments, the tumor is a temozolomide-resistant tumor. In some embodiments, the temozolomide-resistant tumor is a temozolomide-resistant glioblastoma multiforme.

In some embodiments, the therapeutically effective substance is used in the manufacture of a medicament for the treatment of brain cancer such as e.g., glioblastoma multiforme. In some embodiments, the invention provides a therapeutically effective substance for use in the treatment of brain cancer in a patient. In some embodiments, the invention provides a therapeutically effective substance for use in the treatment of glioblastoma multiforme in a patient. In some embodiments, the invention provides a therapeutically effective substance for the treatment of brain cancer in a patient. In some embodiments, the invention provides a therapeutically effective substance for the treatment of brain cancer in a patient.

At 7 days, tumor cell expression of luciferase was seen in both control (C) and aldoxorubicin-treated (T) animals. At 21 days, all control mice had growing tumors, while only 1 aldoxorubicin-treated mouse had detectable tumor. At Day 29, all C mice had died, while only 1 aldoxorubicin-treated mouse was dead and tumor regrowth was observed in 2 mice. At Day 33, 3 T mice had died and tumor had regrown in 4 other mice. † indicates death of the animal.

Figure 5:
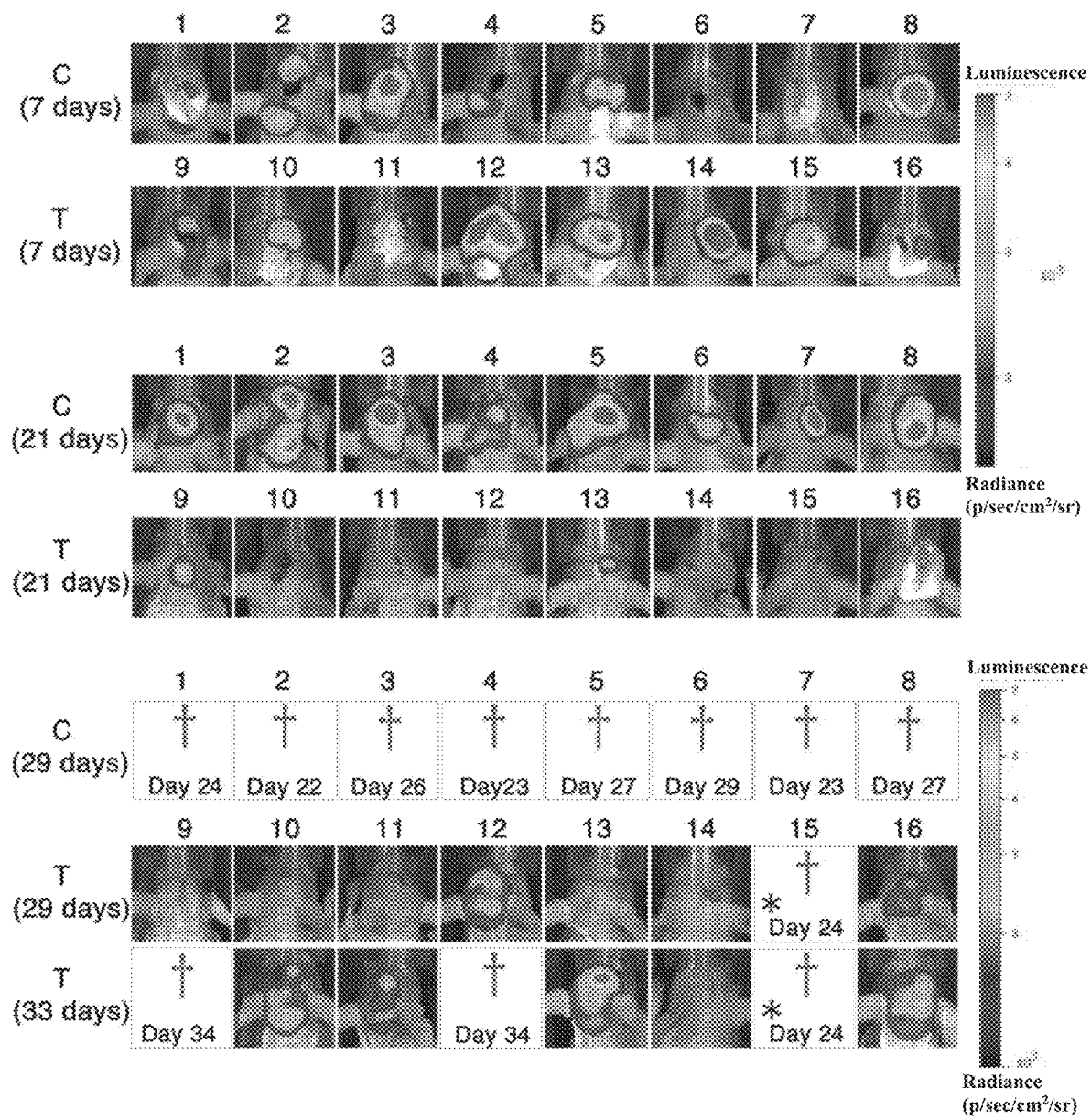
FIG. 5 shows luciferase expression levels in GBM tumors implanted intracranially into mice. Implanted human GBM tumor cells containing the luciferase gene were allowed to grow in the brains of mice for 9 days prior to treatment with either buffer control (C) or aldoxorubicin (T). Mice were administered either buffer (C) or aldoxorubicin on Days 9, 16 and 23. Tumor growth was monitored by detecting bioluminescence of luciferase substrate administered to mice prior to scanning on Days 7, 21, 29 and 33. Intensity of luciferase expression in tumor cells is shown according to the color scheme on the right, with the darkened areas indicating greatest expression (most tumor cells) and black indicating no expression (no tumor cells).
Figure 6:
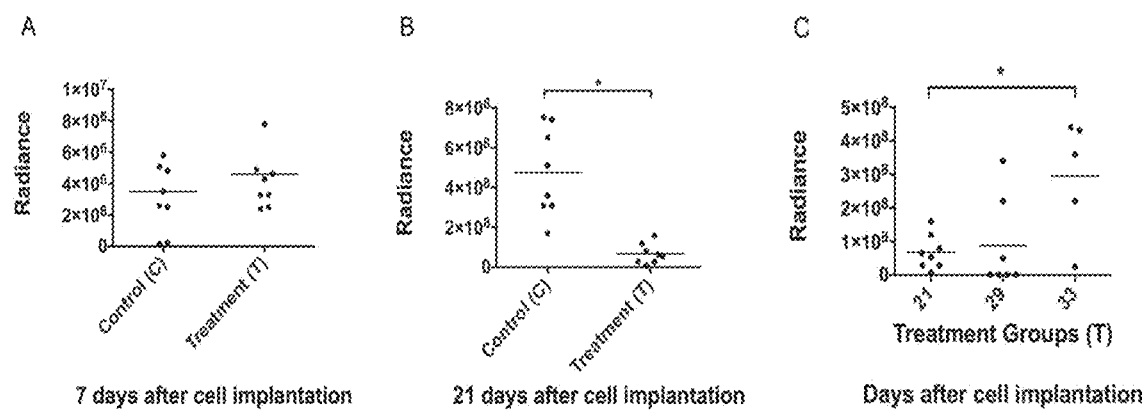

FIG. 6 shows scatter plots for mice in control (C) and aldoxorubicin treatment groups (T) displaying the relationship between tumor sizes expressed as a function of radiance (photons/sec/cm$^2$/sr) obtained from images shown in FIG. 5. There was no relative difference in average tumor sizes between the control group and the treatment group after 7 days (p>0.05) (FIG. 6A), but differences between the control group and the treatment groups after 21 days were observed (p<0.05, see asterisk in FIG. 6B). There was no relative difference in the treatment groups between 21 days to 29 days (p>0.05), but difference was observed at 33 days as a result of the reappearance of the tumors (p<0.05; shown by an asterisk in FIG. 6C).

Figure 7:
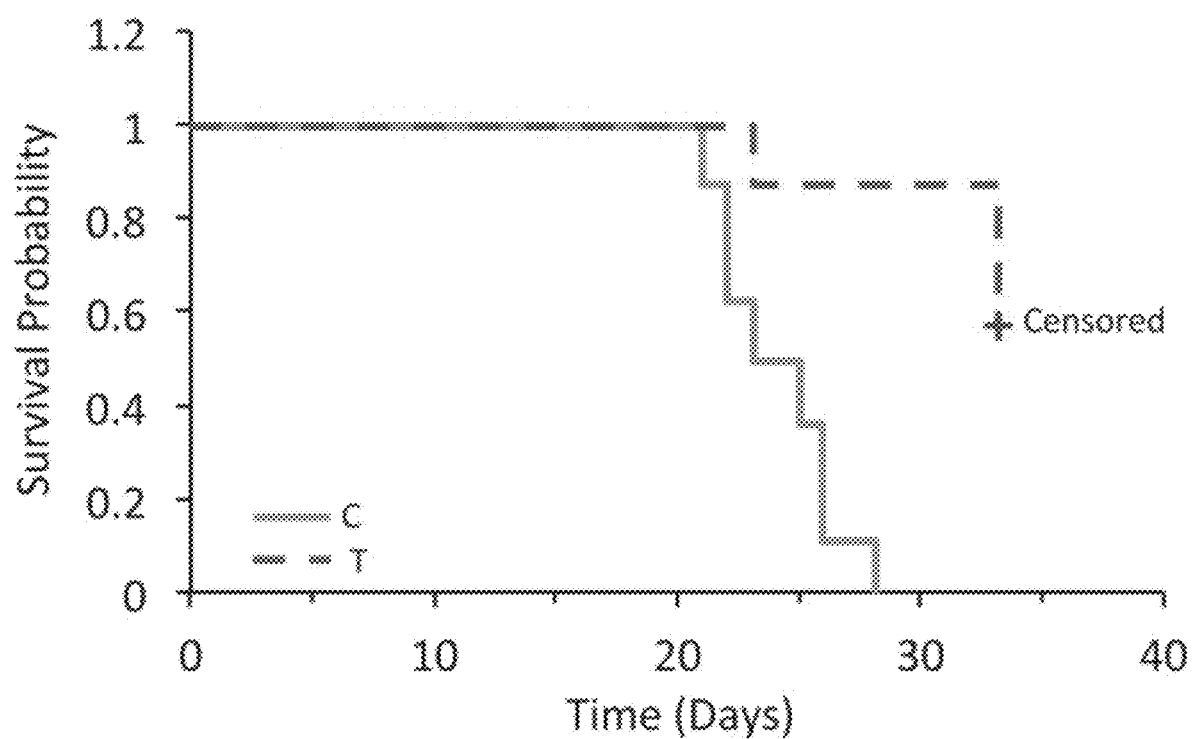

FIG. 7 shows that Kaplan-Meier survival curves by days of study for GBM-bearing mice. Mice receiving aldoxorubicin (n=8; dashed line) survived longer (p=0.0006) than those receiving vehicle (n=8: solid line).

Figure 8:
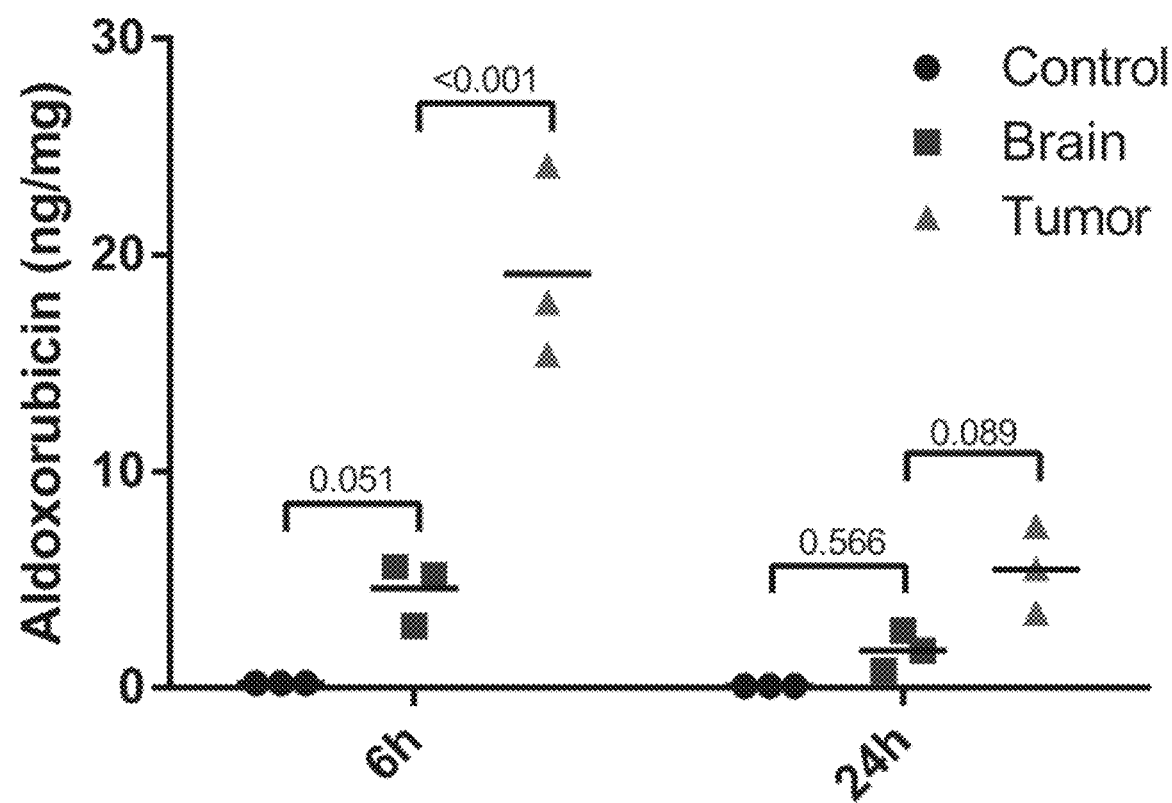

FIG. 8 shows that aldoxorubicin retention was 3- to 4-fold higher in tumor tissues than in the surrounding brain tissues. Aldoxorubicin retention in tumors and surrounding brain tissues of mice was measured by HPLC following intravenous administration of 24 mg/kg dose (75% of the maximum tolerated dose) to intracranial GBM tumor-bearing mice.

Figure 9:
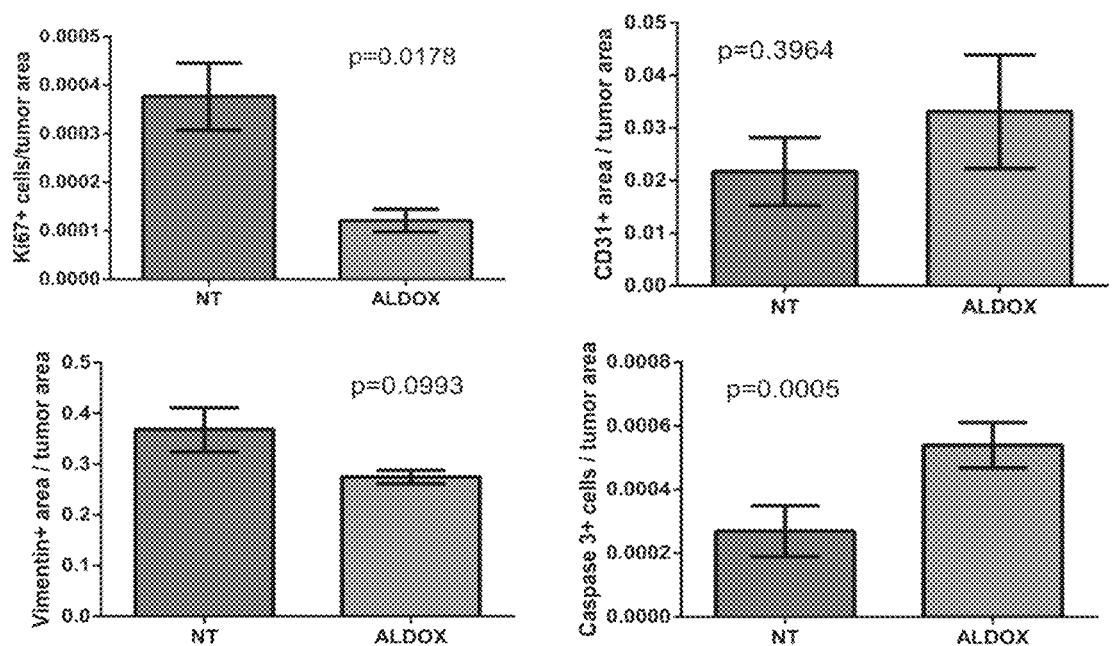

FIG. 9 shows a graphical representation of the immunohistochemical evaluation of aldoxorubicin (ALDOX) treatment on the proliferation (Ki-67), intratumoral vasculature (CD31), intermediate filament protein expression (vimentin), and activation of apoptosis effector (cleaved caspase-3), versus control (NT).

Figure 10:

FIG. 10 shows selective accumulation of aldoxorubicin but not doxorubicin in the intracranial human glioblastoma tumors in athymic nude mice. Tumor-bearing mice received intravenous injections of aldoxorubicin and doxorubicin as described in Example 1. Mice were euthanized 24 h following the last injection. Brains were harvested and imaged using a stereomicroscope equipped for brightfield and epifluorescence at doxorubicin-specific wavelengths to visualize drug accumulation.

Figure 11:
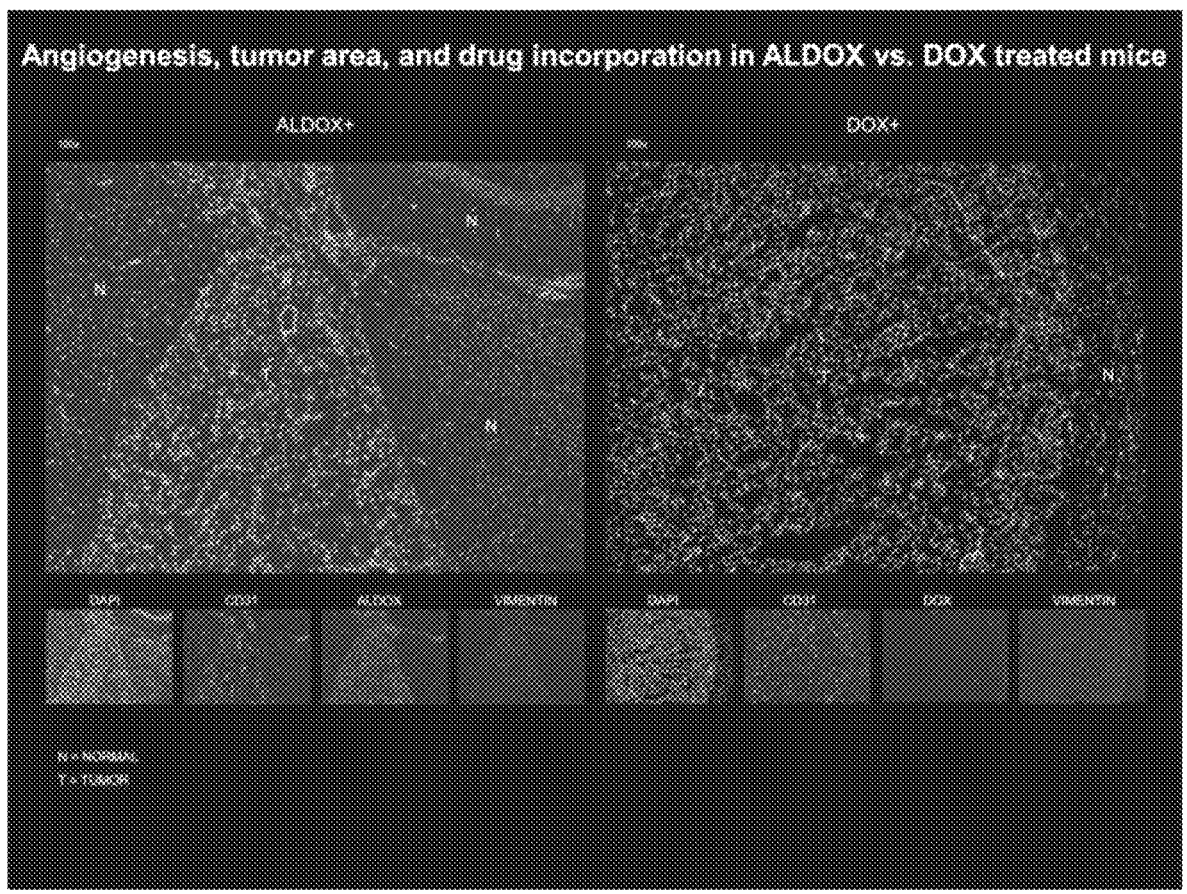

FIG. 11 shows selective accumulation of aldoxorubicin but not doxorubicin as seen in the cryosections of the brain tissues of tumor-bearing mice. Immunohistochemical staining for CD31, a micro-vessel density marker, and Vimentin, a proinvasive type III intermediate filament protein is also shown. All nuclei were counterstained with DAPI.

Figure 1:
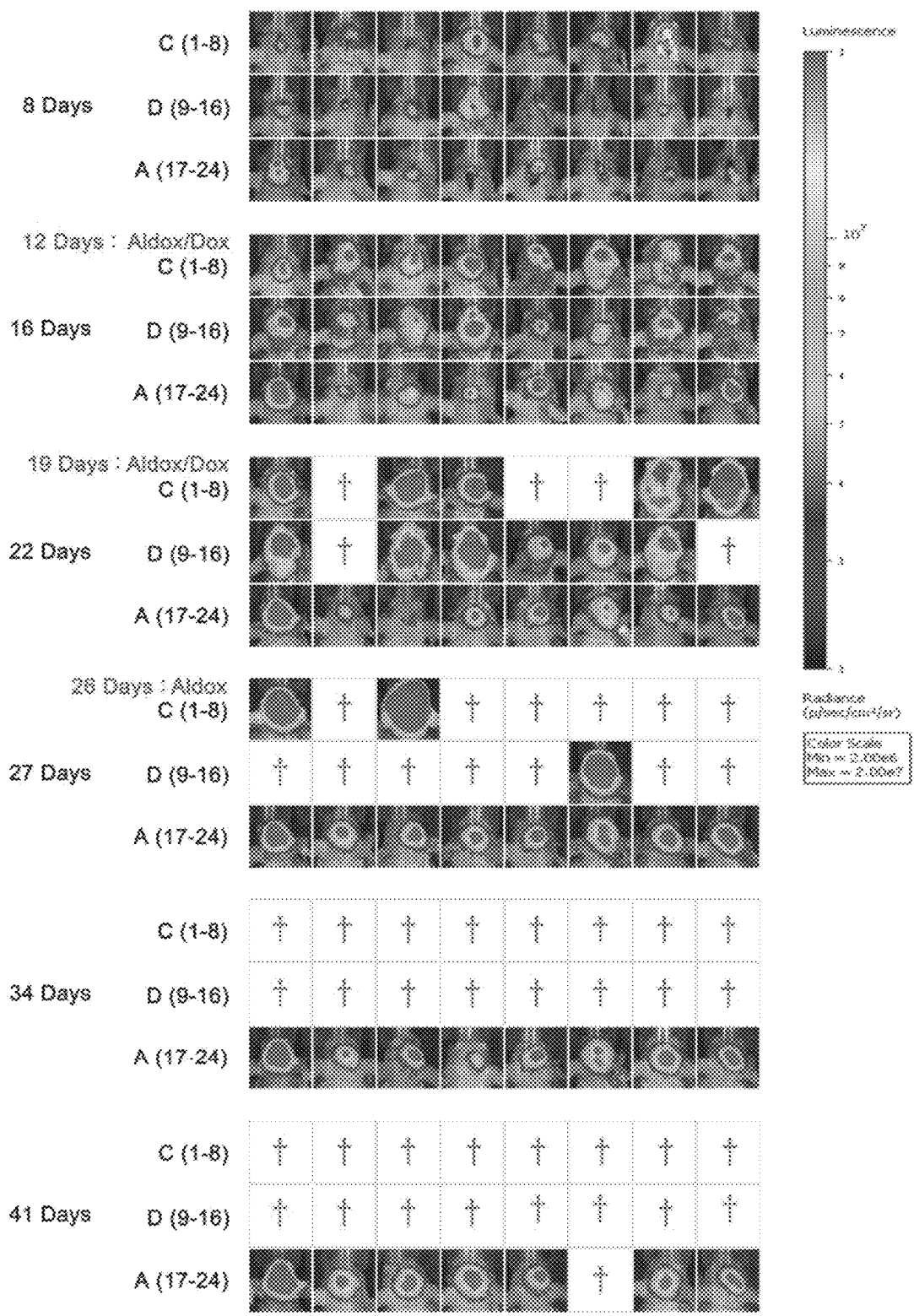
FIG. 1 shows that aldoxorubicin reduces glioblastoma multiforme (GBM) tumor burden in a murine model. Female Balb/c (nu/nu) mice were implanted with $5\times10^5$ firefly luciferase-labeled U87MG (U87-luc) glioma cells intracranially on day 0. After 12 days, control mice in group C (1-8) received tail vein injections of drug vehicle, while mice in the treatment group D (9-16) were injected with 120 μg/injection of doxorubicin (based on a 20 g body weight), and mice in the treatment group A (17-24) received 480 μg/inj of aldoxorubicin. Injection with doxorubicin was repeated after 19 days and with aldoxorubicin after 19 and 26 days. Bioluminescence imaging of brain tumors was performed after 8, 16, 22, 27, 34, and 41 days of tumor cell implantation, and is shown as a function of photon/sec/cm$^2$/sr in each picture (the radiance unit of photons/sec/cm$^2$/sr is the number of photons per second that leave a square centimeter of tissue and radiate into a solid angle of one steradian (sr)). Tumor burden is demonstrated through a colorimetric scale as shown, where the highlighted areas represent the greatest signal intensity (highest tumor burden). \ indicates death of the animal.
Figure 12:
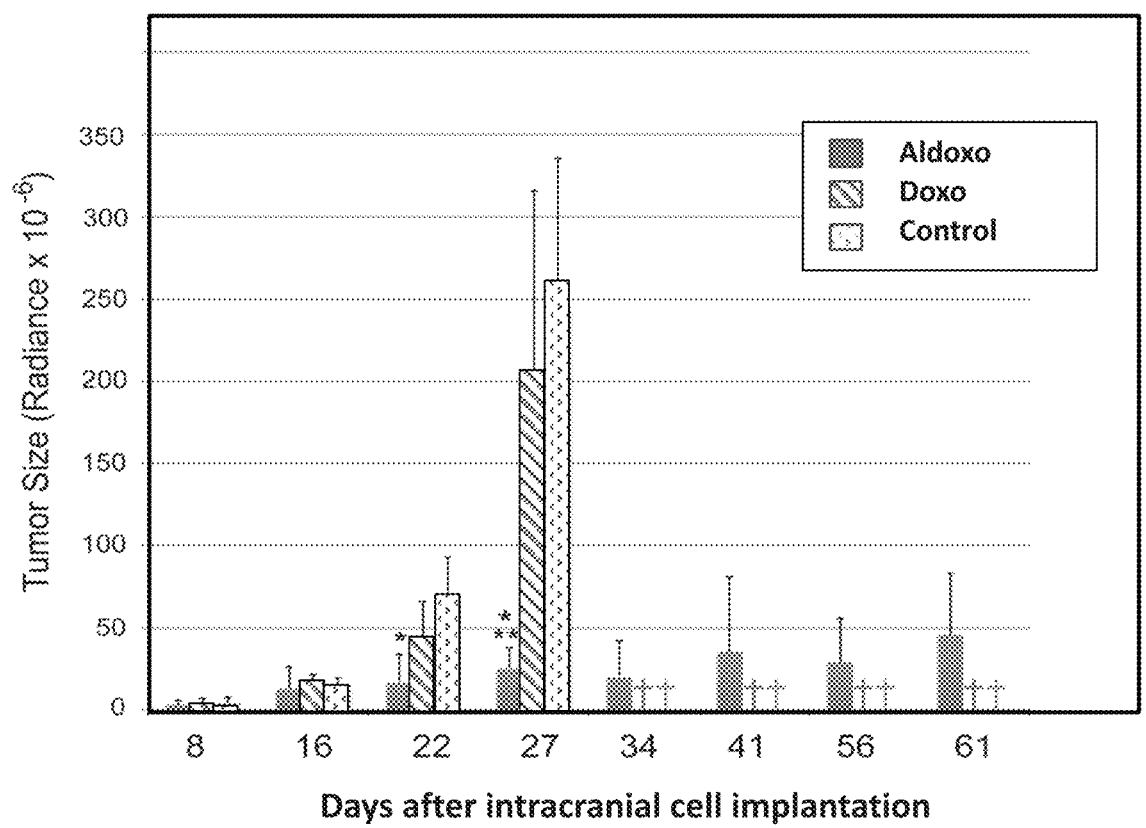

FIG. 12 shows bar graphs for mice in control (control), doxorubicin (doxo), and aldoxorubicin (aldoxo) treatment groups displaying the relationship between tumor sizes expressed as a function of radiance (photons/sec/cm$^2$/sr) obtained from images shown in FIG. 1 and time.

Figure 13:
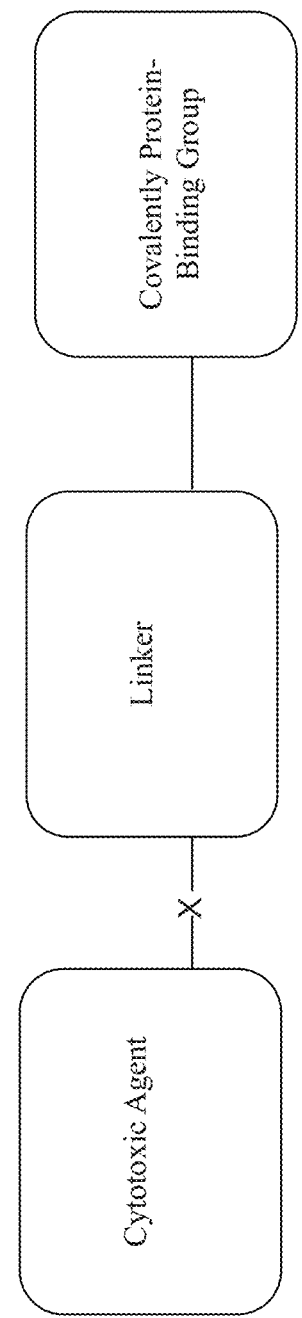

FIG. 13 shows an illustration of the therapeutically effective substance useful in the present invention. X is a bond that can be cleaved hydrolytically or enzymatically in the body of a patient in a pH-dependent manner.

DETAILED DESCRIPTION OF THE INVENTION

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All publications, patents and published patent applications referred to in this application are specifically incorporated by reference herein. In case of conflict, the present specification, including its specific definitions, will control. Unless otherwise specified, it is to be understood that each embodiment of the invention may be used alone or in combination with any one or more other embodiments of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

For a number qualified by the term "about," a variance of 2%, 5% or even 10% is within the scope of the qualified number.

The term "anthracycline" refers to a class of antineoplastic antibiotics having an anthracenedione (also termed anthraquinone or dioxoanthracene) structural unit. For example, the term "anthracycline" is specifically intended to individually include doxorubicin, daunorubicin, epirubicin, idarubicin, valrubicin, pirarubicin, zorubicin, aclarubicin, caminomycin, mitoxantrone, and ametantrone.

The terms "patient" and "individual" are used interchangeably and refer to either a human or a non-human animal. These terms include mammals such as humans, primates, livestock animals (e.g., bovines, porcines), companion animals (e.g., canines, felines) and rodents (e.g., mice and rats).

The term "pharmaceutically acceptable" means a non-toxic material that does not interfere with the effectiveness of the biological activity of the active ingredient(s). The characteristics of the carrier will depend on the route of administration.

The term "pharmaceutically acceptable carrier" refers to a non-toxic carrier that may be administered to a patient, together with a therapeutically effective substance of this invention, and which does not destroy the pharmacological activity of the cytotoxic agent. The term "excipient" refers to an additive in a formulation or composition that is not a pharmaceutically active ingredient.

The term "pharmaceutically effective amount" or "therapeutically effective amount" refers to an amount effective to treat brain cancer in a patient, e.g., effecting a beneficial and/or desirable alteration in the general health of a patient suffering from a disease (e.g., cancer). The skilled worker will recognize that treating brain cancer includes, but is not limited to, killing cancer cells, preventing the growth of new cancer cells, causing tumor regression (a decrease in tumor size), causing a decrease in metastasis, improving vital functions of a patient, improving the well-being of the patient, decreasing pain, improving appetite, improving the patient's weight, and any combination thereof. A "pharmaceutically effective amount" or "therapeutically effective amount" also refers to the amount required to improve the clinical symptoms of a patient. The therapeutic methods or methods of treating brain cancer described herein are not to be interpreted or otherwise limited to "curing" brain cancer.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The term "substituted" refers to moieties having substituents replacing a hydrogen on one or more carbons of the backbone of a chemical compound. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Therapeutically Effective Substance

The therapeutically effective substance useful in the present invention comprises the structure of FIG. 13. or a pharmaceutically acceptable salt thereof, wherein X is a bond that can be cleaved hydrolytically or enzymatically in the body of the patient in a pH-dependent manner.

In some embodiments, the cytotoxic agent used in the therapeutically effective substance is an anthracycline. Anthracyclines include, but are not limited to, doxorubicin, daunorubicin, epirubicin, idarubicin, valrubicin, pirarubicin, zorubicin, aclarubicin, caminomycin, mitoxantrone, and ametantrone, or a derivative thereof. In some embodiments, the anthracycline is doxorubicin or a pharmaceutically acceptable salt, thereof.

In some embodiments, the cleavable moiety ("X") is an acid-cleavable moiety. Acid-cleavable moieties include, but are not limited to, acetal, ketal, imine, hydrazone, carboxylhydrazone or sulphonylhydrazone, or cis-aconityl moieties or moieties containing a substituted or unsubstituted trityl group. In certain embodiments, the acid-cleavable moiety is a hydrazone moiety. In some embodiments, the cytotoxic agent is released when moiety X is cleaved in the body of the patient.

In some embodiments, the cleavable moiety ("X") is enzyme-cleavable. Enzyme-cleavable moieties include, but are not limited to, peptide comprising one or more carbamate bonds. A peptide moiety may comprise, for example, 1-5, 1-10, 1-15, 1-20, 1-25, 1-30, 1-35, 1-40, 2-5, 2-10, 2-15, 2-20, 2-25, 2-30, 2-35, or 2-40 amino acid residues. Peptide moieties include, but are not limited to, moieties comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues. A peptide moiety may be designed to be specifically cleavable by one or more proteases. In some embodiments, the bond being cleaved is a peptide bond, an imide bond, or a carboxyl-hydrazone bond of a hydrazine moiety.

In some embodiments, the linker is an organic molecule. Such linker may comprise at least one aliphatic carbon chain and/or an aliphatic carbon ring with 1-12 carbon atoms, wherein any of the carbon atoms may be substituted with an —OH or =O, and wherein any of the carbon atoms may be replaced with heteroatoms or an aromatic moiety where appropriate and chemically feasible. In some embodiments, the heteroatom is oxygen. In some embodiments, the aliphatic linker may comprise an alkyl chain comprising 1-12 carbon atoms, an alkenyl chain comprising 2-12 carbon atoms, or an alkynyl chain comprising 2-12 carbon atoms, wherein any of the carbon atoms maybe substituted with an —OH or =O, and wherein any of the carbon atoms may be replaced with oxygen atoms where appropriate and chemically feasible. In particular embodiments, the aliphatic linker is an alkyl chain comprising 1-12 carbon atoms, wherein any of the carbon atoms maybe substituted with an =O, where appropriate and chemically feasible. In yet other embodiments, the aliphatic linker is an alkyl chain comprising 3-9, 4-8, or 5-7 carbon atoms, wherein any of the carbon atoms maybe substituted with an =O, where appropriate and chemically feasible. In a particular embodiment, the aliphatic linker is an alkyl chain comprising 6 carbon atoms, wherein the carbon atom attached to the cleavable moiety "X" is substituted with an =O.

The covalently protein-binding group include, but is not limited to, a maleimide group, a haloacetamide group, a haloacetate group, a pyridyldithio group, an N-hydroxysuccinimide ester group, and an isothiocyanate group. In certain embodiments, the covalently protein-binding group is a maleimide group. Covalently protein-binding groups also include a disulfide group, a vinylcarbonyl group, an aziridine group or an acetylene group. A disulfide group may be activated by a thionitrobenzoic acid (e.g. 5'-thio-2-nitrobenzoic acid) as the exchangeable group. A maleimide, pyridyldithio, or N-hydroxysuccinimide ester group can, where appropriate, be substituted by an alkyl group or by the above water-soluble groups. In general, a protein-binding group possesses protein-binding properties, i.e., it binds covalently ("a covalent protein-binding group") or noncovalently ("a noncovalent protein-binding group"), in a physiological environment, to particular amino acids on the surface of the protein. The maleimide group, the haloacetamide group, the haloacetate group, the pyridyldithio group, the disulfide group, the vinylcarbonyl group, the aziridine group, and/or the acetylene group preferably reacts with thiol (—SH) groups of cysteines, while the N-hydroxysuccinimide ester group and/or the isothiocyanate group preferably react with the amino group (—NH) of lysines, on the surface of a protein. For example, the covalently protein-binding group (such as a maleimide group) may bind to albumin. In some embodiments, the albumin is not modified (e.g., it is not modified to be charged, either positively or negatively).

The therapeutically effective substance used in the invention includes any and all combinations of one or more anthracyclines, cleavable moieties, linkers, and covalently protein-binding groups. Therapeutically effective substances may comprise an anthracycline, an acid-cleavable moiety, an alkyl linker, and a covalently protein-binding group. In certain embodiments, the therapeutically effective substance comprises an anthracycline, a hydrazone as the acid-cleavable moiety, an alkyl linker, and a maleimide group as the covalently protein-binding group. In other embodiments, the therapeutically effective substance comprises an anthracycline, a hydrazone moiety as the acid-cleavable moiety, a 6-carbon alkyl linker wherein the carbon atom attached to the cleavable moiety is substituted with an =O, and a maleimide group as the covalently protein-binding group (i.e., an anthracycline-EMCH molecule).

An exemplary compound used in the present invention is DOXO-EMCH. The term "DOXO-EMCH," alone or in combination with any other term, refers to a compound as depicted by the following structure:

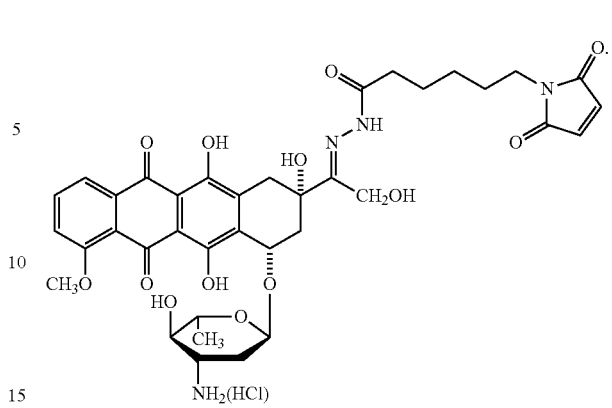

DOXO-EMCH is also referred to as (E)-N'-(1-((2S,4S)-4-(4-amino-5-hydroxy-6-methyl-tetrahydro-2H-pyran-2-yloxy-2,5,12-trihydroxy-7-methoxy-6,11-dioxo1,2,3,4,6,11-hexahydrotetracen-2-yl)-2-hydroxyethylidene)-6-(2,5-dioxo-2H-pyrrol-1(5H)yl)hexanehydrazide.HCl.

Pharmaceutical Compositions

In some embodiments, the invention provides a pharmaceutical composition for use in the treatment of brain cancer in a patient comprising a therapeutically effective substance, wherein the therapeutically effective substance comprises FIG. 13, or a pharmaceutically acceptable salt thereof wherein X is a moiety that can be cleaved hydrolytically or enzymatically in the body of the patient in a pH-dependent manner.

Each of the methods or uses of the present invention, as described herein, comprises administering to a patient a therapeutically effective substance or a pharmaceutically acceptable salt or ester form thereof to treat brain cancer. In some embodiments, the therapeutically effective substance may be administered alone. In some embodiments, the therapeutically effective substance may be administered in combination with an anti-cancer agent. In some embodiments, the therapeutically effective substance may be administered in combination with other medications such as the anthracyclines, platinum-containing anti-cancer compounds, taxanes, alkylating agents, proteasome inhibitors, nucleoside analogs, topoisomerase inhibitors, immunosuppressive agents for the treatment of immune-mediated brain disorders. In some embodiments, the therapeutically effective substance may be administered in combination with other medications such as doxorubicin, cisplatin, carboplatin, paclitaxel, docetaxel, temozolomide, nitrosoureas, bortezomib, gemcitabine, etoposide, topotecan, or a pharmaceutically acceptable salt thereof.

The total amount of a therapeutically effective substance (e.g., DOXO-EMCH) in a composition to be administered to a patient is one that is suitable for that patient. One of skill in the art would appreciate that different individuals may require different total amounts of the therapeutically effective substance. In some embodiments, the amount of the therapeutically effective substance is a pharmaceutically effective amount. The skilled worker would be able to determine the amount of the therapeutically effective substance in a composition needed to treat a patient based on factors such as, for example, the age, weight, and physical condition of the patient. The concentration of therapeutically effective substance (e.g., DOXO-EMCH) depends on its solubility in the intravenous administration solution and the volume of fluid that can be administered. For example, the concentration of the therapeutically effective substance may be from about 0.1 mg/ml to about 50 mg/ml in the injectable composition. In some embodiments, the concentration of the therapeutically effective substance may be from about 0.1 mg/ml to about 25 mg/ml, from about 7 mg/ml to about 17 mg/ml, from about 0.1 mg/ml to about 5 mg/ml, or from about 0.25 mg/ml to about 4.5 mg/ml. In particular embodiments, the concentration of the therapeutically effective substance may be about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, or about 6.0 mg/ml. In some embodiments, the concentration of the therapeutically effective substance may be about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, or about 30 mg/ml.

The pharmaceutical compositions and kits of the present invention may also contain diluents, fillers, salts, buffers, stabilizers, solubilizers, and other materials well known in the art.

The compositions may be administered in a variety of conventional ways. Exemplary routes of administration that can be used include oral, parenteral, intravenous, intra-arterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository. In some embodiments, the compositions are suitable for parenteral administration. These compositions may be administered, for example, intraperitoneally, intravenously, or intrathecally. In some embodiments, the compositions are injected intravenously. In some embodiments, a reconstituted formulation can be prepared by reconstituting a lyophilized anthracycline compound composition in a reconstitution liquid comprising ethanol and water. Such reconstitution may comprise adding the reconstitution liquid and mixing, for example, by swirling or vortexing the mixture. The reconstituted formulation then can be made suitable for injection by mixing e.g., Lactated Ringer's solution with the formulation to create an injectable composition. One of skill in the art would appreciate that a method of administering a therapeutically effective substance formulation or composition would depend on factors such as the age, weight, and physical condition of the patient being treated, and the disease or condition being treated. The skilled worker would, thus, be able to select a method of administration optimal for a patient on a case-by-case basis.

In some embodiments, the composition of the therapeutically effective substance may be used in the manufacture of a medicament for treating brain cancer.

In some embodiments, the present invention provides a kit comprising a therapeutically effective substance as described herein and, a pharmaceutically acceptable excipient, a carrier, and/or a diluent.

In some embodiments, one or more excipients may be included in the composition. One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to empirically determine which excipients, if any, to include in the compositions. Excipients may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier in the compositions.

In some embodiments, a solubilizing agent may be included compositions. Solubilizing agents may be useful for increasing the solubility of any of the components of the composition, including a therapeutically effective substance (e.g., DOXO-EMCH) or an excipient. The solubilizing agents described herein are not intended to constitute an exhaustive list, but are provided merely as exemplary solubilizing agents that may be used in the compositions. In certain embodiments, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

The pH of the compositions may be any pH that provides desirable properties for the formulation or composition. Desirable properties may include, for example, therapeutically effective substance (e.g., DOXO-EMCH) stability, increased therapeutically effective substance retention as compared to compositions at other pHs, and improved filtration efficiency. In some embodiments, the pH of the compositions may be from about 3.0 to about 9.0, e.g., from about 5.0 to about 7.0. In particular embodiments, the pH of the compositions may be 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, or 6.5±0.1.

In some embodiments, it may be beneficial to buffer the pH by including one or more buffers in the compositions. In certain embodiments, a buffer may have a pKa of, for example, about 5.5, about 6.0, or about 6.5. One of skill in the art would appreciate that an appropriate buffer may be chosen for inclusion in compositions based on its pKa and other properties. Buffers are well known in the art. Accordingly, the buffers described herein are not intended to constitute an exhaustive list, but are provided merely as exemplary buffers that may be used in the formulations or compositions of the invention. In certain embodiments, a buffer includes, but is not limited to Tris, Tris HCl, potassium phosphate, sodium phosphate, sodium citrate, sodium ascorbate, combinations of sodium and potassium phosphate, Tris/Tris HCl, sodium bicarbonate, arginine phosphate, arginine hydrochloride, histidine hydrochloride, cacodylate, succinate, 2-(N-morpholino)ethanesulfonic acid (MES), maleate, bis-tris, phosphate, carbonate, and any pharmaceutically acceptable salts and/or combinations thereof.

In some embodiments, a pH-adjusting agent may be included in the compositions. Modifying the pH of a composition may have beneficial effects on, for example, the stability or solubility of a therapeutically effective substance, or may be useful in making a composition suitable for parenteral administration. pH-adjusting agents are well known in the art. Accordingly, the pH-adjusting agents described herein are not intended to constitute an exhaustive list, but are provided merely as exemplary pH-adjusting agents that may be used in the compositions. pH-adjusting agents may include, for example, acids and bases. In some embodiments, a pH-adjusting agent includes, but is not limited to, acetic acid, hydrochloric acid, phosphoric acid, sodium hydroxide, sodium carbonate, and combinations thereof.

In some embodiments, a bulking agent may be included in the compositions. Bulking agents are commonly used in lyophilized compositions to provide added volume to the composition and to aid visualization of the composition, especially in instances where the lyophilized pellet would otherwise be difficult to see. Bulking agents also may help prevent drug loss due to blowout of the active component(s) of a pharmaceutical composition and/or to aid cryoprotection of the composition. Bulking agents are well known in the art. Accordingly, the bulking agents described herein are not intended to constitute an exhaustive list, but are provided merely as exemplary bulking agents that may be used in the compositions.

Exemplary bulking agents may include carbohydrates, monosaccharides, disaccharides, polysaccharides, sugar alcohols, amino acids, and sugar acids, and combinations thereof. Carbohydrate bulking agents include, but are not limited to, mono-, di-, or poly-carbohydrates, starches, aldoses, ketoses, amino sugars, glyceraldehyde, arabinose, lyxose, pentose, ribose, xylose, galactose, glucose, hexose, idose, mannose, talose, heptose, glucose, fructose, methyl a-D-glucopyranoside, maltose, lactone, sorbose, erythrose, threose, arabinose, allose, altrose, gulose, idose, talose, erythrulose, ribulose, xylulose, psicose, tagatose, glucosamine, galactosamine, arabinans, fructans, fucans, galactans, galacturonans, glucans, mannans, xylans, inulin, levan, fucoidan, carrageenan, galactocarolose, pectins, amylose, pullulan, glycogen, amylopectin, cellulose, pustulan, chitin, agarose, keratin, chondroitin, dermatan, hyaluronic acid, xanthin gum, sucrose, trehalose, dextran, and lactose. Sugar alcohol bulking agents include, but are not limited to, alditols, inositols, sorbitol, and mannitol. Amino acid bulking agents include, but are not limited to, glycine, histidine, and proline. Sugar acid bulking agents include, but are not limited to, aldonic acids, uronic acids, aldaric acids, gluconic acid, isoascorbic acid, ascorbic acid, glucaric acid, glucuronic acid, gluconic acid, glucaric acid, galacturonic acid, mannuronic acid, neuraminic acid, pectic acids, and alginic acid.

In some embodiments, a surfactant may be included in the compositions. Surfactants, in general, reduce the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the formulations or compositions of the invention. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof.

In some embodiments, an encapsulating agent may be included in the compositions. Encapsulating agents can sequester molecules and help stabilize or solubilize them. Encapsulating agents are well known in the art. Accordingly, the encapsulating agents described herein are not intended to constitute an exhaustive list, but are provided merely as exemplary encapsulating agents that may be used in the compositions. Encapsulating agents that may be included in compositions include, but are not limited to, dimethyl-β-cyclodextrin, hydroxyethyl-β-cyclodextrin, hydroxypropyl-β-cyclodextrin, and trimethyl-β-cyclodextrin, and combinations thereof.

In some embodiments, a tonicity-adjusting agent may be included in the compositions. The tonicity of a liquid composition is an important consideration when administering the composition to a patient, for example, by parenteral administration. Tonicity-adjusting agents, thus, may be used to help make a composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the compositions. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

In some embodiments, a stabilizing agent may be included in the compositions. Stabilizing agents help increase the stability of a therapeutically effective substance in the compositions. This may occur by, for example, reducing degradation or preventing aggregation of a therapeutically effective substance. Without wishing to be bound by theory, mechanisms for enhancing stability may include sequestration of the therapeutically effective substance from a solvent or inhibiting free radical oxidation of the anthracycline compound. Stabilizing agents are well known in the art. Accordingly, the stabilizing agents described herein are not intended to constitute an exhaustive list, but are provided merely as exemplary stabilizing agents that may be used in the compositions. Stabilizing agents may include, but are not limited to, emulsifiers and surfactants.

In some embodiments, a protectant may be included in the compositions. Protectants are agents that protect a pharmaceutically active ingredient (e.g., a therapeutically effective substance) from an undesirable condition (e.g., instability caused by freezing or lyophilization, or oxidation). Protectants can include, for example, cryoprotectants, lyoprotectants, and antioxidants. Cryoprotectants are useful in preventing loss of potency of an active pharmaceutical ingredient (e.g., an anthracycline compound) when a composition is exposed to a temperature below its freezing point. For example, a cryoprotectant could be included in a reconstituted lyophilized formulation so that the formulation could be frozen before dilution for intravenous (IV) administration. Cryoprotectants are well known in the art. Accordingly, the cryoprotectants described herein are not intended to constitute an exhaustive list, but are provided merely as exemplary cryoprotectants that may be used in the compositions. Cryoprotectants include, but are not limited to, solvents, surfactants, encapsulating agents, stabilizing agents, viscosity modifiers, and combinations thereof. Cryoprotectants may include, for example, disaccharides (e.g., sucrose, lactose, maltose, and trehalose), polyols (e.g., glycerol, mannitol, sorbitol, and dulcitol), glycols (e.g., ethylene glycol, polyethylene glycol and propylene glycol).

Lyoprotectants are useful in stabilizing the components of a composition. For example, a therapeutically effective substance could be lyophilized with a lyoprotectant prior to reconstitution. Lyoprotectants are well known in the art. Accordingly, the lyoprotectants described herein are not intended to constitute an exhaustive list, but are provided merely as exemplary lyoprotectants that may be used in the compositions. Lyoprotectacts include, but are not limited to, solvents, surfactants, encapsulating agents, stabilizing agents, viscosity modifiers, and combinations thereof. Exemplary lyoprotectants may be, for example, sugars and polyols. Trehalose, sucrose, dextran, and hydroxypropyl-beta-cyclodextrin are non-limiting examples of lyoprotectants.

Antioxidants are useful in preventing oxidation of the components of a composition. Oxidation may result in aggregation of a drug product or other detrimental effects to the purity of the drug product or its potency. Antioxidants are well known in the art. Accordingly, the antioxidants described herein are not intended to constitute an exhaustive list, but are provided merely as exemplary antioxidants that may be used in the compositions. Antioxidants may be, for example, sodium ascorbate, citrate, thiols, metabisulfite, and combinations thereof.

In some embodiments, a viscosity modifying agent may be included in the composition. Viscosity modifiers change the viscosity of liquid compositions. This may be beneficial because viscosity plays an important role in the ease with which a liquid composition is filtered. A composition may be filtered prior to lyophilization and reconstitution, or after reconstitution. Viscosity modifiers are well known in the art. Accordingly, the viscosity modifiers described herein are not intended to constitute an exhaustive list, but are provided merely as exemplary viscosity modifiers that may be used in the compositions. Viscosity modifiers include solvents, solubilizing agents, surfactants, and encapsulating agents. Exemplary viscosity modifiers that may be included in compositions include, but are not limited to, N-acetyl-DL-tryptophan and N-acetyl-cysteine.

Methods of Treatment

The methods of treatment provided herein are useful for a variety of clinical applications. Anthracyclines are useful in the treatment of cancer. For example, doxorubicin is an intercalating agent as well as a topoisomerase II inhibitor, and preferentially kills rapidly dividing cells, such as tumor cells. DOXO-EMCH is an anthracycline compound that can be used to treat solid tumors as well as hematological malignancies. DOXO-EMCH acts by covalently binding to albumin wherein the free thiol of cysteine-34 of albumin binds the DOXO-EMCH maleimide via a Michael addition. It is believed that DOXO-EMCH-albumin conjugate then circulates in the bloodstream until reaching a tumor, where the lower pH in the tumor results in cleavage of the hydrazone bond between doxorubicin and the EMCH moiety, thereby releasing the doxorubicin.

In one aspect, the invention provides methods for treating brain cancer. In some embodiments, the cancer is a primary brain cancer. Examples of a primary brain cancer include glioma, astrocytoma, oligodendroglioma, ependymoma, meningioma, craniopharyngioma, germinoma, pineocytoma, pineoblastoma and glioblastoma multiforme. In some embodiments, the primary brain cancer is glioblastoma multiforme. In some embodiments, the cancer is a metastatic or secondary brain cancer. Examples of metastatic or secondary brain cancers include a solid tumor cancer, breast cancer, lung cancer, endometrial cancer, ovarian cancer, pancreatic cancer, pancreatic ductal adenocarcinoma, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma multiforme, prostate cancer, liver cancer, bone cancer, chondrosarcoma, renal cancer, bladder cancer, and gastric cancer. In some embodiments, the metastatic or secondary brain cancer is glioblastoma multiforme. In some embodiments, the cancer is a temozolomide-resistant cancer. In some embodiments, the temozolomide-resistant cancer is a temozolomide-resistant glioblastoma multiforme.

In another aspect, the invention provides methods for treating a primary brain tumor. In some embodiments, the primary brain tumor is glioblastoma multiforme. In other embodiments, the brain cancer is a metastatic brain tumor. In some embodiments, the metastatic tumor is from a cancer including but not limited to breast cancer, lung cancer, stomach cancer, endometrial cancer, ovarian cancer, pancreatic cancer, pancreatic ductal adenocarcinoma, cancer of the adrenal cortex, non-Hodgkin's lymphoma, multiple myeloma, leukemia, Kaposi's sarcoma, Ewing's sarcoma, soft tissue sarcoma, nephroblastoma, glioblastoma, prostate cancer, liver cancer, bone cancer, chondrosarcoma, renal cancer, bladder cancer, thyroid cancer and gastric cancer. In some embodiments, the tumor is a temozolomide-resistant tumor. In some embodiments, the temozolomide-resistant tumor is a temozolomide-resistant glioblastoma multiforme.

In some embodiments, the method comprises administering DOXO-EMCH (i.e., aldoxorubicin) either alone or in combination with an anti-cancer agent for treating cancers or tumors. In some embodiments, the method comprises administering DOXO-EMCH (i.e., aldoxorubicin) either alone or in combination with an anti-cancer agent for treating temozolomide-resistant tumors. In some embodiments, the method comprises administering DOXO-EMCH (i.e., aldoxorubicin) for treating temozolomide-resistant tumors or cancers. In some embodiments, the method comprises administering DOXO-EMCH (i.e., aldoxorubicin) for treating glioblastoma multiforme. In other embodiments, the method comprises administering DOXO-EMCH (i.e., aldoxorubicin) for treating temozolomide-resistant glioblastoma multiforme.

Variations and Modifications

Variations, modifications, and other implementations of what is described herein will occur to those of ordinary skill without departing from the spirit and the scope of the invention. Accordingly, the invention is not to be limited to the preceding description or the following examples.

Exemplification

With aspects of the invention now being generally described, these will be more readily understood by reference to the following examples, which are included merely for purposes of illustration of certain features and embodiments of the invention and are not intended to be limiting.

Equivalents

Those skilled in the art will recognize, or be able to ascertain using no more than routine experimentation, numerous equivalents to the compounds, compositions, and methods of use thereof described herein. Such equivalents are considered to be within the scope of the invention.

EXAMPLES

The preclinical efficacy of doxorubicin versus aldoxorubicin was compared in an in vivo mouse model for glioblastoma.

Example 1: Aldoxorubicin, but not Doxorubicin, Induces Tumor Regression and Significantly Increases Survival in Xenograft Mouse Model Intracranial implantation of U87-luc glioma cells in mice: A U87MG subline, U87-luc with a luciferase reporter gene was used for establishing intracranial human glioblastoma tumors. Female BALB/c (nu/nu) mice, 6-8 weeks of age, were anesthetized with a ketamine/xylazine cocktail solution. Animals were secured in a Harvard Apparatus stereotaxic head frame, a 1 cm midline scalp incision was made, and $5\times10^5$ cells in 5 μL serum-free DMEM were injected into the left striatum (coordinates: 2.5 mm lateral and 0.5 mm posterior to the bregma) through a burr hole in the skull using a 10 μl Hamilton syringe to deliver tumor cells to a 3.5 mm intraparenchymal depth. The burr hole in the skull was sealed with bone wax and the incision closed using wound glue. Tumor growth was evaluated by bioluminescent imaging.

Aldoxorubicin treatment of mice: The study consisted of 8 vehicle-treated control mice (group C), 8 doxorubicin-treated mice (group D), and 8 aldoxorubicin-treated mice (group A). Treatment was initiated twelve days after intracranial implantation of glioblastoma multiforme (GBM) cells. Vehicle (10 mM sodium phosphate, 5% D-(+)-glucose, pH 6.4) or aldoxorubicin was administered intravenously for a total of six injections (i.e., 12, 19, 26, 42, 50, and 56, days after cell implantation). All the doses were ~75% of the maximum tolerated dose (MTD) of 32 mg/kg/inj in mice except that the dose given after 50 days of cell implantation was 50% of the MTD. Doxorubicin was administered intravenously for a total of two injections (i.e., 12 and 19 days after cell implantation) with ~75% of the MTD of 8 mg/kg/inj. Both the drugs and the vehicle were administered using an injection volume of 0.15 ml.

In vivo imaging of intracranial tumors: Intracranial tumor growth was quantified by bioluminescent imaging using an in vivo imaging system (Xenogen, Palo Alto, Calif.). All mice were given an IP injection of 100 μl of 30 mg/ml D-luciferin (PerkinElmer) suspended in DPBS 10 minutes before imaging to provide a substrate for the luciferase enzyme. Prior to imaging, mice were anesthetized with inhalation of isoflurane gas. Images were captured using the Xenogen Ivis 200 imaging system and quantified with Living Image 4.1 software from Xenogen for a region of interest that encompassed the head of the mouse. Image intensities were expressed as photons/sec/cm$^2$/sr.

HPLC System and Conditions: An Agilent 1100 Series HPLC System (Wilmington, Del., USA) having a scanning fluorescent detector with excitation and emission wavelengths set at 480 and 560 nm, respectively, was used. Agilent Chemstation software was used for data acquisition. Separation was achieved on a Waters Spherisorb ODS2 column (4 mm×250 mm, 5 μm) fitted with a guard cartridge (BDS-Hypersil-C18, 5 μM). Elution was performed with mobile phase containing 65% monosodium phosphate, pH 2.2, and 35% acetonitrile. A constant flow rate of 1.25 ml/min was used for the separation. The column was set to 28° C. and the injection volume was 25 μl.

Doxorubicin, aldoxorubicin, and the internal standard daunorubicin demonstrated average retention times of 4.06, 4.39 and 6.52 min., respectively, and were sufficiently resolved under the applied assay conditions. In the organ samples analyzed, aldoxorubicin eluted with the retention time of doxorubicin. No interfering peaks were observed under the chromatography conditions used.

Sample preparation: Aldoxorubicin, 24 mg/kg/inj (75% of the MTD), was administered in intracranial GBM tumor-bearing mice through tail vein injection, and after 4, 8, 16, and 24 h after injection, mice (3 animals at each time point) were euthanized by $CO_2$ gas. Blood samples were collected by heart puncture in heparinized tubes, and centrifuged for plasma separation. Immediately after blood sampling, organs (brain, heart, kidney liver and lung) were surgically removed. The plasma and tissues were stored at −80° C. until analysis.

Frozen samples were thawed at room temperature and homogenized in sterile saline using a PowerGen Model 125 homogenizer (Fisher Scientific) to obtain final tissue concentrations (w/v) of 150 mg/ml for the liver and brain; 125 mg/ml for the lung, heart and muscle; and 100 mg/ml for kidney. Perchloric acid (35%, v/v) was added to a 20 μl aliquot of plasma or tissue samples followed by 25 μl of mobile phase. The samples were vortexed followed by centrifugation at 10,000×g for 10 min. and 25 μl of the supernatant was applied to the HPLC column.

Statistical Analysis: The log-rank test was used to create Kaplan-Meier survival curves to compare survival between control and drug-treated mice using the Statistical Analysis Software of SAS Institute, Inc., Cary, N.C. Differences between groups were assessed using the unpaired Student's t test. AR values are shown as the mean±standard deviation. A p value≤0.05 was considered statistically significant.

Results

Figure 2:
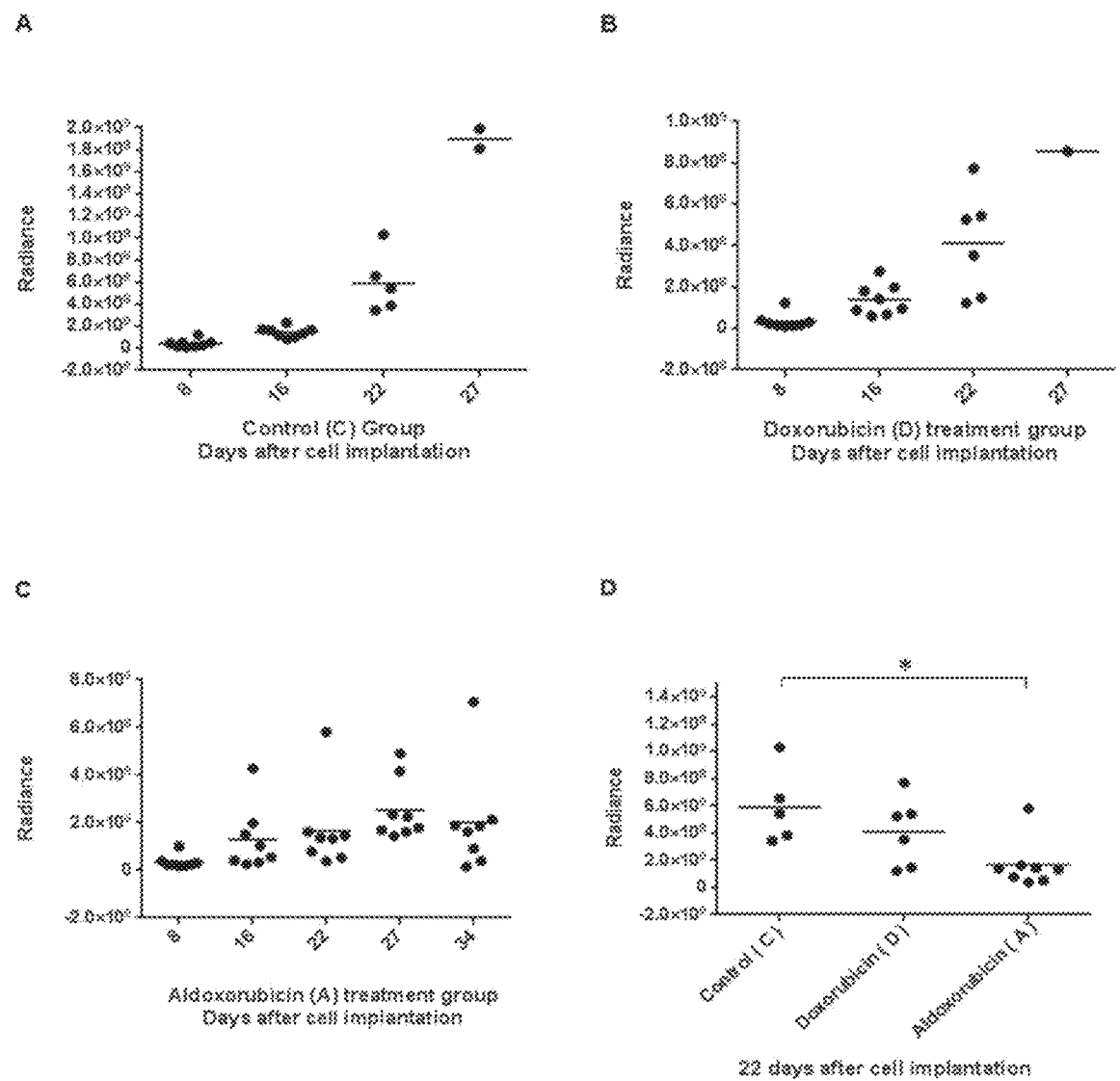
FIG. 2 shows scatter plots for mice in control (C) and treatment groups doxorubicin (D) and aldoxorubicin (A) displaying the relationship between tumor sizes expressed as a function of radiance (photons/sec/cm$^2$/sr) obtained from images shown in FIG. 1. There was no relative difference in average tumor sizes between the control and the treatment groups after 8 days of cell implantation (p>0.05) (compare Figure A, B, and C). Difference between the control group and the aldoxorubicin group, but not the doxorubicin group, was observed 22 days after implantation (p=0.005; shown by an asterisk, FIG. 2D). There was no relative difference in tumor growth between 8 days and 22 days in the aldoxorubicin group (p>0.05) (FIG. 2C). However, a relative difference in tumor growth between 8 and 22 days was observed in the doxorubicin group (p<0.05) (FIG. 2B), indicating suppression of tumor growth by aldoxorubicin but not doxorubicin.

Aldoxorubicin but not doxorubicin is a potent inhibitor of glioma tumors in mice. FIGS. 1 and 2 show that there was no relative difference in average tumor sizes between the control group (group C), doxorubicin treatment group (group D) and the aldoxorubicin treatment group (group A) after 8 days of intracranial tumor cell implantation (p>0.05). 3 animals in the control group and 2 in the doxorubicin group died and others developed large tumors in 22 days, Aldoxorubicin treatment for 2 weeks showed tumor regression resulting in average tumor size of 28% that of the control group and 40% that of doxorubicin treatment group (FIG. 2D). Further, animals in the control and doxorubicin treatment groups experienced much shorter survival compared to animals in the aldoxorubicin treatment group. All animals in the control group (group C) and doxorubicin group (group D) died within 34 days after tumor implantation, but animals in the treatment group (group A) remained alive. Even after 41 days, seven of the eight animals in the aldoxorubicin group were still alive. See FIG. 1.

Figure 3:
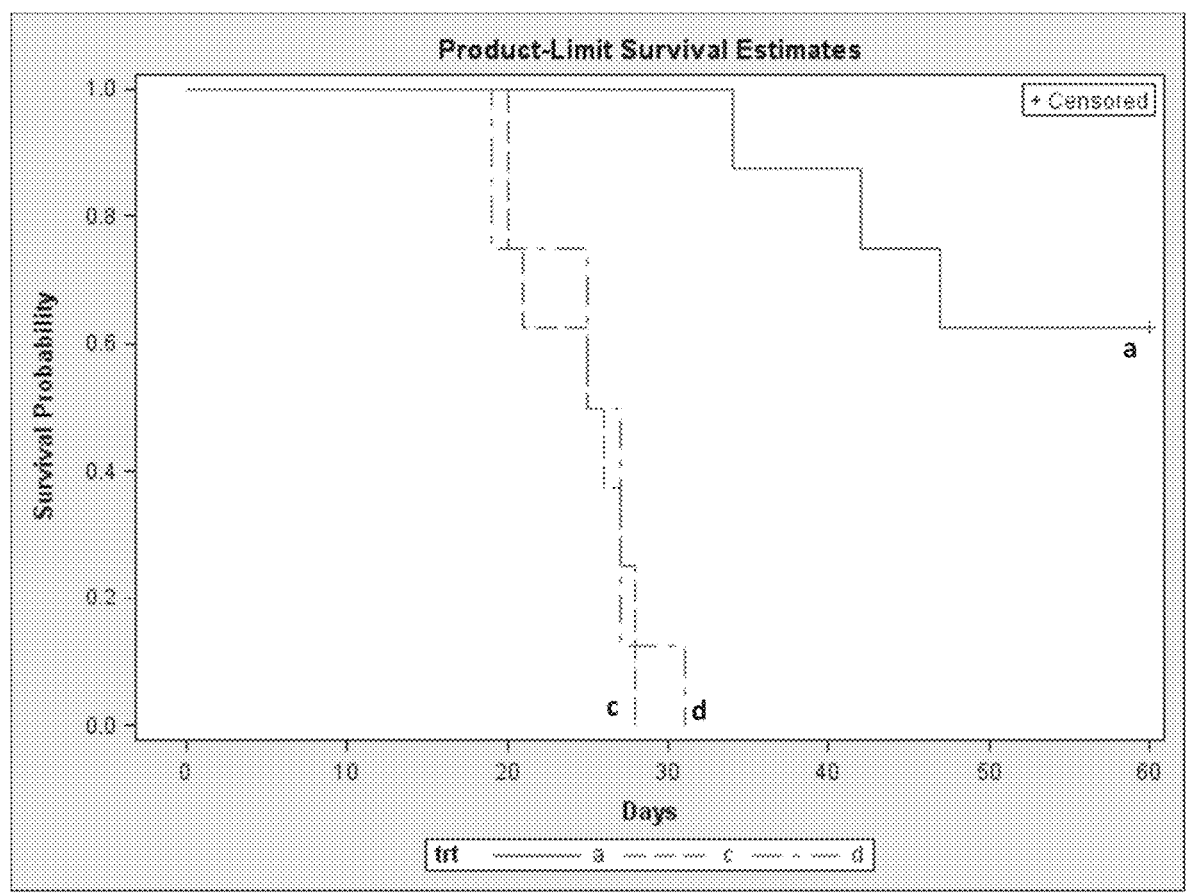
FIG. 3 shows Kaplan-Meier survival curves by days of study for GBM-bearing mice. Mice receiving aldoxorubicin treatment (n=8; solid line (d)) survived a longer time (p≤0.0001) than mice receiving vehicle (dashed line labelled (c)) or doxorubicin (dashed line labelled (d)). There was no difference in the survival curves between vehicle-treated and doxorubicin-treated mice (p=0.949). As described herein, aldoxorubicin was administered intravenously for a total of six injections (i.e., 12, 19, 26, 42, 50, and 56 days after cell implantation). All the doses were ~75% of the maximum tolerated dose (MTD) of 32 mg/kg/injection, except that the dose given after 50 days of cell implantation was 50% of the MTD. Doxorubicin was administered for a total of two injections (i.e., 12 and 19 days after cell implantation) with ~75% of the MTD of 8 mg/kg/injection.

FIG. 3 features Kaplan-Meier survival curves showing increased survival times (p<0.0001) in mice treated with aldoxorubicin as compared with the vehicle-treated or the doxorubicin-treated group. There was no difference in the survival time between the vehicle-treated and the doxorubicin-treated mice (p=0.949). When the study was terminated, the surviving animals were censored because they had not reached the endpoint.

Figure 4:
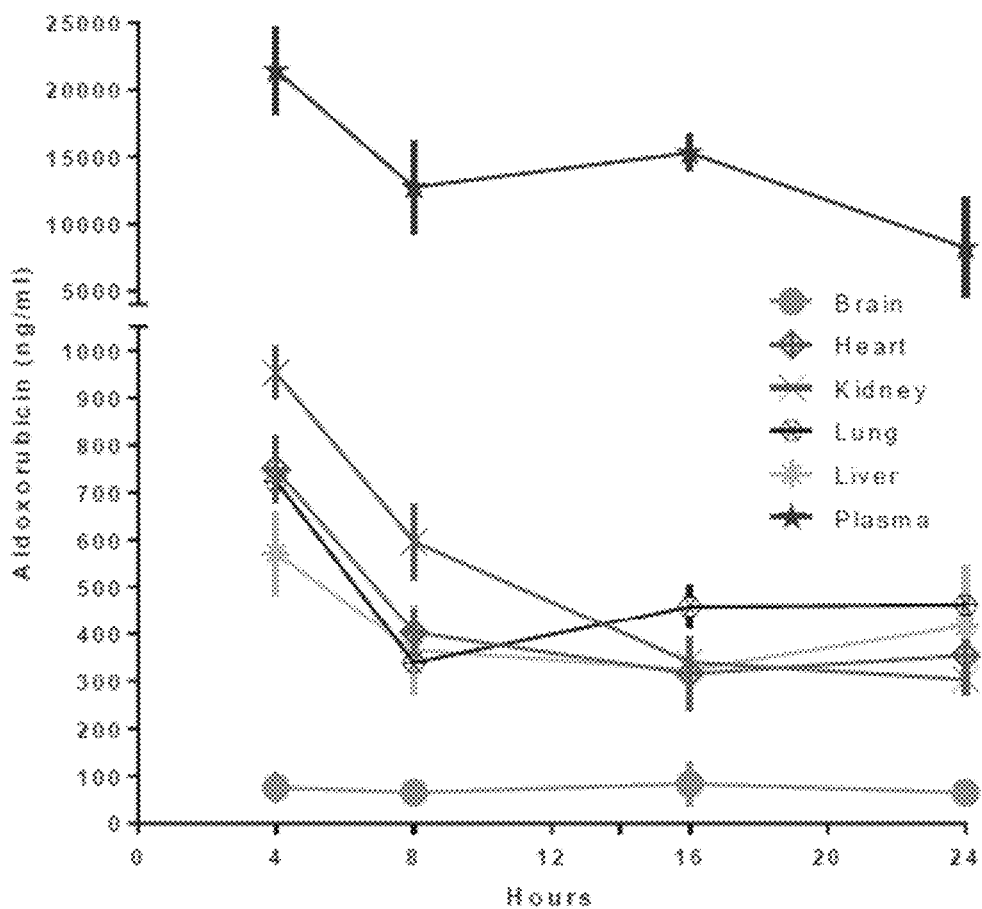
FIG. 4 shows the concentration-time profile of aldoxorubicin in various tissues following intravenous administration of 24 mg/kg dose (75% of the maximum tolerated dose) to intracranial GBM tumor-bearing mice. Lines represent the mean data (ng of aldoxorubicin/ml of plasma or tissues extracts) obtained from three mice sampled at each time point. Bars indicate ±standard deviation. Aldoxorubicin concentrations in brain represent values obtained from total brain tissues from tumor-bearing mice.

HPLC was used to determine the plasma and tissue distribution of aldoxorubicin its administration to intracranial tumor-bearing mice. The concentration vs. time profile is shown in FIG. 4. After intravenous administration of aldoxorubicin (~75% of the MTD), the drug concentrations were the highest after 4 h in plasma and other organs except brain. Plasma concentration was more than 20 fold higher than the mean concentration in liver, heart, lung and kidney, and more than 200 fold higher when compared to that in the brain. The prodrug reached nearly 50% of its concentration in 20 h in plasma and in other tissues except in the brain. In the brain, the levels remained almost same from 4 h to 24 h, suggesting that the high antitumor activity in brain may be associated with prolonged presence of the drug.

Conclusions

These results demonstrate that aldoxorubicin, but not doxorubicin, administered intravenously induces tumor regression and significantly increases survival in an in vivo xenograft model employing intracranial implantation of human GBM tumors.

Example 2: Aldoxorubicin-Induced Tumor Regression and Increase of Survival in Xenograft Mouse Model Female mice (6-8 weeks of age) were implanted intracranially with U87-luc subline with luciferase reporter gene to establish human glioblastoma tumors. Tumor growth was evaluated by bioluminescent imaging using D-luciferin substrate. 8 mice were treated with aldoxorubicin and 8 were treated with phosphate buffer saline (vehicle). Treatment started 9 days after implantation of the GBM cells. Aldoxorubicin or vehicle was administered i.v. once a week for three weeks (9, 16, and 23 days after cell implantation). The first two doses of aldoxorubicin were 75% and the third dose was 50% of the MTD of 32 mg/kg/injection in mice. Results are shown in FIG. 5.

Conclusions

These results demonstrate that aldoxorubicin administered intravenously induces tumor regression and increases survival in an in vivo xenograft model employing intracranial implantation of human GBM tumors.

Example 3: Aldoxorubicin Retention in Tumor Tissues

HPLC System and Conditions: The HPLC system used was an Agilent 1100 Series (Wilmington, Del., USA) equipped with a scanning fluorescent detector with excitation and emission wavelengths set at 480 and 560 nm, respectively. Agilent Chemstation software was used for data acquisition. Separation was achieved on a Waters Spherisorb ODS2 column (4 mm×250 mm, 5 µm) fitted with a guard cartridge (BDS-Hypersil-C18, 5 µM). Elution was performed with mobile phase comprised of 65% 50 mM monosodium phosphate, pH 2.2, and 35% acetonitrile. A constant flow rate of 1.25 ml/min was used for the separation. The column was set to 28° C. and the injection volume was 25 µl.

Doxorubicin, aldoxorubicin, and the internal standard daunorubicin demonstrated average retention times of 4.06, 4.39 and 6.52 min, respectively, and were sufficiently resolved under the applied assay conditions. In the organ samples analyzed, aldoxorubicin eluted with the retention time of doxorubicin. No interfering peaks were observed under the chromatography conditions used.

Sample preparation: For quantification of aldoxorubicin in brain tissue and brain tumors, mice were euthanized by $CO_2$ inhalation 6 and 24 h after aldoxorubicin injection (24 mg/kg/inj), brains were harvested and tumors were resected. The harvested tissues were stored at −80° C. until analysis.

Frozen samples were thawed at room temperature and homogenized in sterile saline using a PowerGen Model 125 homogenizer (Fisher Scientific) to obtain final tissue concentrations (w/v) of 150 mg/ml. Perchloric acid (35%, v/v) was then added to a 2.0 µl aliquot followed by 25 µl of mobile phase. The samples were vortexed followed by centrifugation at 10,000×g for 10 min and 2.5 µl of the supernatant was applied to the HPLC column. In the tissue samples analyzed, aldoxorubicin eluted with the retention time of doxorubicin.

Conclusions

Aldoxorubicin retention was 3- to 4-fold higher in tumor tissues than in the surrounding brain tissues. See FIG. 8.

Example 4: Short Description of the Experiment

Immunohistochemistry: For histologic analysis, brain tissues from control and drug-treated tumor-bearing mice were harvested, snap frozen in optimal cutting temperature (OCT) compound and stored at −80° C. Cryostat sections were placed on slides and fixed in zinc-buffered formalin. Slides were blocked with 5% goat serum in 1% BSA followed by overnight incubation with primary antibodies against CD31 (102402, Biolegend, San Diego, Calif.), Ki-67 (ab156956, Abcam, Cambridge, Mass.), Vimentin (ab92547, Abcam), cleaved-Caspase-3 (CP229B, Biocare Medical), and GFAP (NB300-141, Novus Biologicals, Littleton, Colo.). Slides were then incubated with primary antibody source-specific secondary antibodies conjugated to Alexa Fluor 488 or 635 and DAN as a nuclear counterstain. The detection fluorophores used were limited to those around the inherent fluorescence spectra of doxorubicin ($\lambda_{ex}$=480 nm, $\lambda_{em}$=550-590 nm) (22876313) to avoid bleed-through and enable co-detection of the drug with respect to certain antigens. Epifluorescence photomicrographs were captured at 100× and 400× magnification using an FV1000 confocal microscope (Olympus of America, Center Valley, Pa.) equipped with multi-Argon, 405, 559, and 635 diodes. Quantitative analysis was performed with Slidebook software (Intelligent Imaging Innovations, Denver, Colo.). FIGS. 9 and 11 illustrate the quantitative analyses of the data obtained by immunohistochemical analysis.

Conclusions

Aldoxorubicin accumulates in the brain tumor but not in normal brain tissue. Doxorubicin is not found in any appreciable amount in either the tumor or normal brain.

Example 5: Short Description of the Experiment

Aldoxorubicin/doxorubicin detection in brain tumors: Tumor-bearing mice were given intravenous injections of aldoxorubicin or doxorubicin as described above in Example 1. Mice were euthanized 24 h following the last injection. Brains were harvested and imaged using an MVX10 stereomicroscope (Olympus of America) equipped for brightfield and epifluorescence with filters encompassing doxorubicin-specific wavelengths to visualize drug accumulation. See FIG. 10.

Conclusions

Aldoxorubicin and not doxorubicin accumulates in glioblastoma tumors.

The invention claimed is:

1. A pharmaceutical composition comprising a therapeutically effective substance for use in the treatment of brain cancer, wherein the therapeutically effective substance comprises DOXO-EMCH or a pharmaceutically acceptable salt thereof, wherein the therapeutically effective substance binds to serum albumin, and wherein the composition further comprises sodium bicarbonate and tert-butyl alcohol.

2. The pharmaceutical composition according to claim 1, wherein the brain cancer is a primary brain cancer.

3. The pharmaceutical composition according to claim 2, wherein the primary brain cancer is glioma, astrocytoma, oligodendroglioma, ependymoma, meningioma, craniopharyngioma, germinoma, pineocytoma, pineoblastoma and glioblastoma multiforme.

4. The pharmaceutical composition according to claim 3, wherein the primary brain cancer is glioblastoma multiforme.

5. The pharmaceutical composition according to claim 1, wherein the brain cancer is a secondary or metastatic cancer.

6. The pharmaceutical composition according to claim 5, wherein the secondary or metastatic cancer is selected from bladder cancer, breast cancer, lung cancer, stomach cancer, endometrial cancer, ovarian cancer, pancreatic cancer, pancreatic ductal adenocarcinoma, cancer of the adrenal cortex, non-Hodgkin's lymphoma, multiple myeloma, leukemia, Kaposi's sarcoma, Ewing's sarcoma, soft tissue sarcoma, nephroblastoma, prostate cancer, liver cancer, bone cancer, chondrosarcoma, renal cancer, bladder cancer, thyroid cancer and gastric cancer.

7. The pharmaceutical composition according to claim 1, wherein the composition further comprises an anti-cancer agent.

8. The pharmaceutical composition according to claim 7, wherein the anti-cancer agent is selected from doxorubicin, cisplatin, carboplatin, paclitaxel, docetaxel, temozolomide, nitrosoureas, bortezomib, gemcitabine, etoposide, topotecan, or a pharmaceutically acceptable salt thereof.

9. The pharmaceutical composition according to claim 1, wherein the therapeutically effective substance is (E)-N'-(1-((2S,4S)-4-(4-amino-5-hydroxy-6-methyl-tetrahydro-2H-pyran-2-yloxy)-2,5,12-trihydroxy-7-methoxy-6,11-dioxo-1,2,3,4,6,11-hexahydrotetracen-2-yl)-2-hydroxyethylidene)-6-(2,5-dioxo-2H-pyrrol-1(5H)yl)hexanehydrazide.HCl.

* * * * *